United States Patent
Howard et al.

(10) Patent No.: US 8,295,944 B2
(45) Date of Patent: Oct. 23, 2012

(54) ELECTRODE ARRAY WITH ELECTRODES HAVING CUTOUT PORTIONS AND METHODS OF MAKING THE SAME

(75) Inventors: Joshua Dale Howard, Granada Hills, CA (US); Anne Margaret Pianca, Santa Monica, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 97 days.

(21) Appl. No.: 12/945,657

(22) Filed: Nov. 12, 2010

(65) Prior Publication Data

US 2011/0130816 A1 Jun. 2, 2011

Related U.S. Application Data

(60) Provisional application No. 61/265,249, filed on Nov. 30, 2009.

(51) Int. Cl.
*A61N 1/00* (2006.01)
(52) U.S. Cl. ........................................................ 607/116
(58) Field of Classification Search .................. 607/16, 607/116; 29/847, 882
See application file for complete search history.

(56) References Cited

U.S. PATENT DOCUMENTS

| | | |
|---|---|---|
| 4,112,953 A | 9/1978 | Shanker et al. |
| 4,350,159 A | 9/1982 | Gouda |
| 4,471,777 A | 9/1984 | McCorkle, Jr. |
| 4,565,200 A | 1/1986 | Cosman |
| 4,577,643 A | 3/1986 | Beranek |
| 4,630,611 A | 12/1986 | King |
| 4,668,221 A | 5/1987 | Luther |
| 4,744,370 A | 5/1988 | Harris |
| 4,886,065 A | 12/1989 | Collins, Jr. |
| 4,931,056 A | 6/1990 | Ghajar et al. |
| 4,955,891 A | 9/1990 | Carol |
| 5,006,122 A | 4/1991 | Wyatt et al. |
| 5,114,424 A | 5/1992 | Hagen et al. |
| 5,116,345 A | 5/1992 | Jewell et al. |
| 5,300,080 A | 4/1994 | Clayman et al. |
| 5,303,704 A | 4/1994 | Molacek |
| 5,318,041 A | 6/1994 | DuBois et al. |
| 5,330,485 A | 7/1994 | Clayman et al. |

(Continued)

FOREIGN PATENT DOCUMENTS

EP  1062973 A1  12/2000

(Continued)

OTHER PUBLICATIONS

"System and Method for Selective Multi-site Microelectrode Recording," IP.com, IPCOM000016587D, Jul. 1, 2003.

(Continued)

*Primary Examiner* — George Manuel
*Assistant Examiner* — Robert N Wieland
(74) *Attorney, Agent, or Firm* — Frommer Lawrence & Haug LLP; Bruce E Black

(57) ABSTRACT

A lead for brain stimulation includes a lead body having a distal end. At least one cable extends within the lead body, each cable comprising at least one conductor. The lead further includes a plurality of electrodes coupled to the at least one cable. Each of the plurality of electrodes defines a cutout portion that receives and attaches to a one of the at least one cable.

20 Claims, 12 Drawing Sheets

U.S. PATENT DOCUMENTS

| | | | |
|---|---|---|---|
| 5,411,025 A | 5/1995 | Webster, Jr. | |
| 5,450,846 A | 9/1995 | Goldreyer | |
| 5,458,629 A * | 10/1995 | Baudino et al. | 607/116 |
| 5,522,874 A | 6/1996 | Gates | |
| 5,618,287 A | 4/1997 | Fogarty et al. | |
| 5,628,313 A | 5/1997 | Webster, Jr. | |
| 5,711,316 A | 1/1998 | Elsberry et al. | |
| 5,713,922 A | 2/1998 | King | |
| 5,728,148 A | 3/1998 | Bostrom et al. | |
| 5,752,937 A | 5/1998 | Otten et al. | |
| 5,782,239 A | 7/1998 | Webster, Jr. | |
| 5,843,148 A | 12/1998 | Gijsbers et al. | |
| 5,913,882 A | 6/1999 | King | |
| 5,925,073 A | 7/1999 | Chastain et al. | |
| 5,938,688 A | 8/1999 | Schiff | |
| 5,978,713 A | 11/1999 | Prutchi et al. | |
| 6,011,996 A | 1/2000 | Gielen et al. | |
| 6,026,567 A | 2/2000 | Swoyer et al. | |
| 6,066,165 A | 5/2000 | Racz | |
| 6,167,311 A | 12/2000 | Rezai | |
| 6,181,971 B1 | 1/2001 | Doan | |
| 6,261,300 B1 | 7/2001 | Carol et al. | |
| 6,301,492 B1 | 10/2001 | Zonenshayn | |
| 6,343,226 B1 | 1/2002 | Sunde et al. | |
| 6,413,263 B1 | 7/2002 | Lobdill et al. | |
| 6,416,520 B1 | 7/2002 | Kynast et al. | |
| 6,456,869 B1 | 9/2002 | Raylman et al. | |
| 6,456,889 B2 | 9/2002 | Pianca et al. | |
| 6,510,347 B2 | 1/2003 | Borkan | |
| 6,529,774 B1 | 3/2003 | Greene | |
| 6,572,624 B2 | 6/2003 | U et al. | |
| 6,575,968 B1 | 6/2003 | Eggers et al. | |
| 6,597,954 B1 | 7/2003 | Pless et al. | |
| 6,687,549 B1 | 2/2004 | Helland et al. | |
| 6,757,970 B1 | 7/2004 | Kuzma et al. | |
| 6,782,292 B2 | 8/2004 | Whitehurst | |
| 6,849,062 B2 | 2/2005 | Kantor | |
| 7,033,326 B1 | 4/2006 | Pianca et al. | |
| 7,047,084 B2 | 5/2006 | Erickson et al. | |
| 7,174,219 B2 | 2/2007 | Wahlstrand et al. | |
| 7,177,701 B1 | 2/2007 | Pianca | |
| 7,177,702 B2 | 2/2007 | Wallace et al. | |
| 7,212,867 B2 | 5/2007 | Van Venrooij et al. | |
| 7,668,601 B2 | 2/2010 | Hegland et al. | |
| 7,761,985 B2 | 7/2010 | Hegland et al. | |
| 8,000,808 B2 | 8/2011 | Hegland et al. | |
| 2001/0027336 A1 | 10/2001 | Gielen et al. | |
| 2002/0151924 A1 | 10/2002 | Shiber | |
| 2002/0183817 A1 | 12/2002 | Van Venrooij et al. | |
| 2003/0212446 A1 | 11/2003 | Kaplan et al. | |
| 2004/0059392 A1 | 3/2004 | Parramon et al. | |
| 2004/0122499 A1 | 6/2004 | Westlund | |
| 2004/0199235 A1 | 10/2004 | Younis | |
| 2005/0004637 A1 | 1/2005 | Singhal et al. | |
| 2005/0015130 A1 | 1/2005 | Gill | |
| 2005/0021118 A1 * | 1/2005 | Genau et al. | 607/116 |
| 2005/0070983 A1 | 3/2005 | Rugnetta et al. | |
| 2005/0203600 A1 | 9/2005 | Wallace et al. | |
| 2005/0203602 A1 | 9/2005 | Wallace et al. | |
| 2005/0222647 A1 | 10/2005 | Wahlstrand et al. | |
| 2006/0025841 A1 | 2/2006 | McIntyre | |
| 2006/0095088 A1 | 5/2006 | De Ridder | |
| 2006/0100671 A1 | 5/2006 | Ridder | |
| 2006/0116742 A1 | 6/2006 | De Ridder | |
| 2006/0149335 A1 | 7/2006 | Meadows | |
| 2006/0149336 A1 | 7/2006 | Meadows | |
| 2006/0168805 A1 | 8/2006 | Heglund et al. | |
| 2006/0173262 A1 | 8/2006 | Heglund et al. | |
| 2006/0247697 A1 | 11/2006 | Sharma et al. | |
| 2006/0259110 A1 | 11/2006 | Wallace et al. | |
| 2007/0150034 A1 | 6/2007 | Rooney et al. | |
| 2007/0203540 A1 | 8/2007 | Goetz et al. | |
| 2007/0203542 A1 | 8/2007 | Goetz et al. | |
| 2007/0203543 A1 | 8/2007 | Stone et al. | |
| 2007/0203546 A1 * | 8/2007 | Stone et al. | 607/59 |
| 2007/0213795 A1 | 9/2007 | Bradley et al. | |
| 2008/0103572 A1 | 5/2008 | Gerber | |
| 2008/0147158 A1 | 6/2008 | Zweber et al. | |
| 2008/0243218 A1 | 10/2008 | Bottomley et al. | |
| 2009/0204193 A1 | 8/2009 | Kokones et al. | |
| 2010/0076535 A1 | 3/2010 | Pianca et al. | |
| 2010/0268298 A1 | 10/2010 | Moffitt et al. | |
| 2011/0004267 A1 | 1/2011 | Meadows | |
| 2011/0005069 A1 | 1/2011 | Pianca | |
| 2011/0078900 A1 | 4/2011 | Pianca et al. | |
| 2011/0130803 A1 | 6/2011 | McDonald | |
| 2011/0130817 A1 | 6/2011 | Chen | |
| 2011/0130818 A1 | 6/2011 | Chen | |
| 2011/0238129 A1 | 9/2011 | Moffitt et al. | |
| 2011/0313500 A1 | 12/2011 | Barker et al. | |
| 2012/0016378 A1 | 1/2012 | Pianca et al. | |
| 2012/0046710 A1 | 2/2012 | DiGiore et al. | |
| 2012/0071949 A1 | 3/2012 | Pianca et al. | |

FOREIGN PATENT DOCUMENTS

| | | |
|---|---|---|
| EP | 0879016 B1 | 10/2003 |
| EP | 1935448 | 6/2008 |
| WO | 9936122 A1 | 7/1999 |
| WO | 2004002288 A2 | 1/2004 |
| WO | 2005092432 A1 | 10/2005 |
| WO | 2006047265 | 5/2006 |
| WO | 2006083881 A1 | 8/2006 |
| WO | 2006083884 A1 | 8/2006 |
| WO | 2005102446 A1 | 11/2006 |
| WO | 2006133445 A2 | 12/2006 |
| WO | 2007097860 A1 | 8/2007 |
| WO | 2007097873 A1 | 8/2007 |
| WO | 2007100427 A1 | 9/2007 |
| WO | 2007100428 A1 | 9/2007 |
| WO | 2008115426 A1 | 9/2008 |

OTHER PUBLICATIONS

"Universal Instrument Guide and Surgical Insertion Tool for Stereotactic Frames," IP.com, IPCOM000011023D, Feb. 7, 2003.
International Search Report and Written Opinion for International Patent Application No. PCT/US2009/057953, mailed Apr. 21, 2010.
U.S. Appl. No. 13/275,112, filed Oct. 17, 2011.
U.S. Appl. No. 13/363,059, filed Jan. 31, 2012.
U.S. Appl. No. 13/368,982, filed Feb. 8, 2012.
U.S. Appl. No. 13/369,013, filed Feb. 8, 2012.
U.S. Appl. No. 13/368,733, filed Feb. 8, 2012.

* cited by examiner

ELECTRODE ARRAY WITH ELECTRODES HAVING CUTOUT PORTIONS AND METHODS OF MAKING THE SAME

CROSS-REFERENCE TO RELATED APPLICATIONS

This application claims the benefit under 35 U.S.C. §119 (e) of U.S. Provisional Patent Application Ser. No. 61/265,249 filed on Nov. 30, 2009, which is incorporated herein by reference.

FIELD

The invention is directed to devices and methods for brain stimulation including deep brain stimulation. In addition, the invention is directed to devices and method for brain stimulation using a lead having a plurality of electrodes comprising cutout portions.

BACKGROUND

Deep brain stimulation can be useful for treating a variety of conditions including, for example, Parkinson's disease, dystonia, essential tremor, chronic pain, Huntington's Disease, levodopa-induced dyskinesias and rigidity, bradykinesia, epilepsy and seizures, eating disorders, and mood disorders. Typically, a lead with a stimulating electrode at or near a tip of the lead provides the stimulation to target neurons in the brain. Magnetic resonance imaging (MRI) or computerized tomography (CT) scans can provide a starting point for determining where the stimulating electrode should be positioned to provide the desired stimulus to the target neurons.

Upon insertion, current is introduced along the length of the lead to stimulate target neurons in the brain. This stimulation is provided by electrodes, typically in the form of rings, disposed on the lead. The current projects from each electrode similarly and in all directions at any given length along the axis of the lead. Because of the shape of the electrodes, radial selectivity of the current is minimal. This results in the unwanted stimulation of neighboring neural tissue, undesired side effects and an increased duration of time for the proper therapeutic effect to be obtained.

In the field of deep brain stimulation, radially segmented electrode arrays (RSEA) have been developed to provide superior radial selectivity of current. Radially segmented electrode arrays are useful for deep brain stimulation because the target structures in the deep brain are often not symmetric about the axis of the distal electrode array. In some cases, a target may be located on one side of a plane running through the axis of the lead. In other cases, a target may be located at a plane that is offset at some angle from the axis of the lead. Thus, radially segmented electrode arrays may be useful for selectively simulating tissue. These radially segmented arrays may be made using electrodes in the form of portions of electrodes having cutouts.

BRIEF SUMMARY

In some embodiments, a lead for brain stimulation includes a lead body having a distal end. At least one cable extends within the lead body. Each cable includes at least one conductor. The lead further includes a plurality of electrodes coupled to the at least one cable. Each of the plurality of electrodes defines a cutout portion that receives and attaches to a one of the at least one cable.

In another embodiment, a lead for brain stimulation includes a plurality of stimulating units. Each of the plurality of stimulating units includes at least one cable extending within the lead body. Each cable includes at least one conductor. A plurality of electrodes are coupled to the at least one cable. Each of the plurality of electrodes comprises at least a portion of a sphere and a cutout portion that receives and attaches to a one of the at least one cable. A lead body is formed about each of the plurality of stimulating units.

In yet another embodiment, a method of manufacturing a device for brain stimulation includes forming at least one cable having at least one conductor. A plurality of electrodes are coupled to the at least one cable. Each of the plurality of electrodes includes at least a portion of a sphere and defines a cutout portion that receives and attaches to a one of the at least one cable. A lead body is formed over the at least one cable.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of devices and methods for brain stimulation including deep brain stimulation. In addition, the invention is directed to devices and method for brain stimulation using a lead having a plurality of electrodes comprising portions of spheres and cutout portions.

A lead for deep brain stimulation may include stimulation electrodes, recording electrodes, or a combination of both. A practitioner may determine the position of the target neurons using the recording electrode(s) and then position the stimulation electrode(s) accordingly without removal of a recording lead and insertion of a stimulation lead. In some embodiments, the same electrodes can be used for both recording and stimulation. In some embodiments, separate leads can be used; one with recording electrodes which identify target neurons, and a second lead with stimulation electrodes that replaces the first after target neuron identification. A lead may include recording electrodes spaced around the circumference of the lead to more precisely determine the position of the target neurons. In at least some embodiments, the lead is rotatable so that the stimulation electrodes can be aligned with the target neurons after the neurons have been located using the recording electrodes.

Deep brain stimulation devices and leads are described in the art. See, for instance, U.S. Patent Publication 2006/0149335 A1 ("Devices and Methods For Brain Stimulation"), and co-pending patent application U.S. Ser. No. 12/237,888 ("Leads With Non-Circular-Shaped Distal Ends For Brain Stimulation Systems and Methods of Making and Using"). Each of these references is incorporated herein by reference in its respective entirety.

Figure 12:
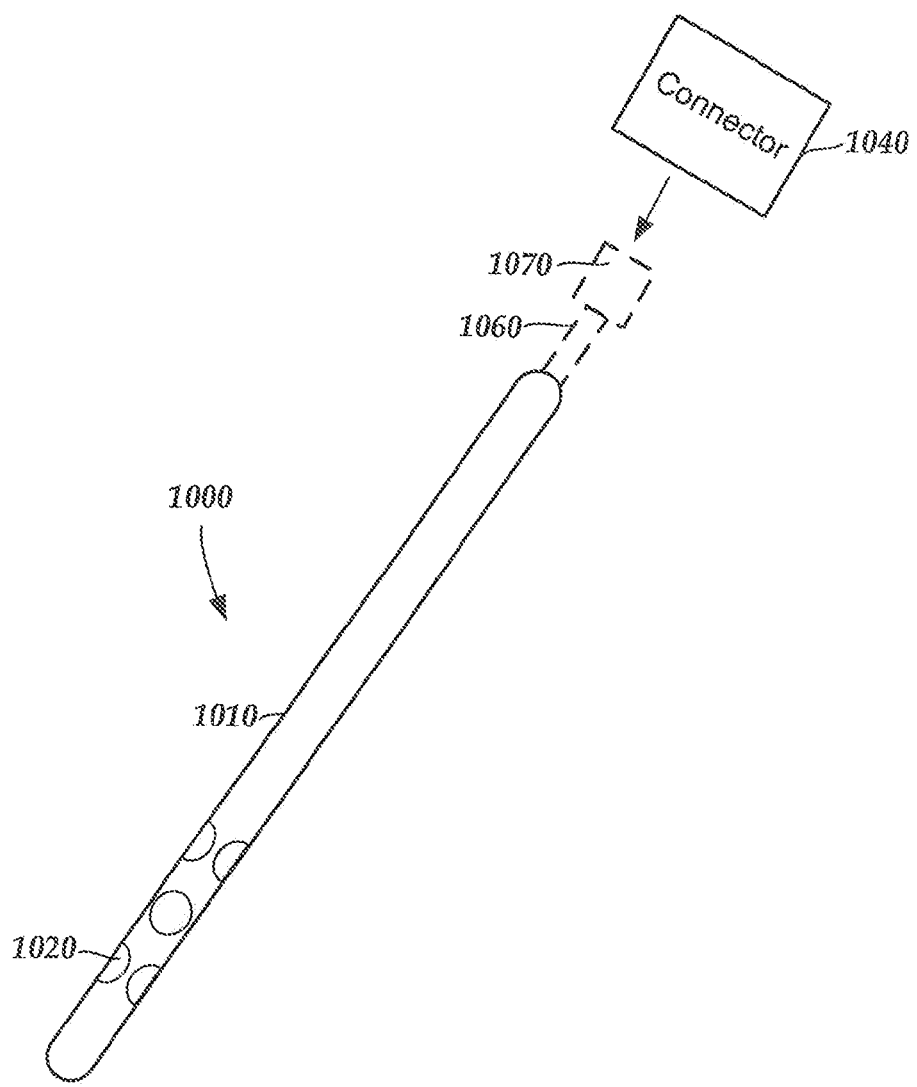
FIG. 12 is a schematic side view of one embodiment of a device for brain stimulation, according to the invention.

FIG. 12 illustrates one embodiment of a device for brain stimulation. The device includes a lead 100, segmented electrodes 1020, a connector 1040 for connection of the electrodes to a control unit, and a stylet 1050 for assisting in insertion and positioning of the lead in the patient's brain. The stylet 1050 can be made of a rigid material. Examples of suitable materials include tungsten, stainless steel, or plastic. The stylet 1050 may have a handle 1060 to assist insertion into the lead, as well as rotation of the stylet 1050 and lead 1000.

In one example of operation, access to the desired position in the brain can be accomplished by drilling a hole in the patient's skull or cranium with a cranial drill (commonly referred to as a burr), and coagulating and incising the dura mater, or brain covering. The lead 100 can be inserted into the cranium and brain tissue with the assistance of the stylet 1050. The lead can be guided to the target location within the brain using, for example, a stereotactic frame and a microdrive motor system. In some embodiments, the microdrive motor system can be fully or partially automatic. The microdrive motor system may be configured to perform one or more the following actions (alone or in combination): rotate the lead, insert the lead, or retract the lead. In some embodiments, measurement devices coupled to the muscles or other tissues stimulated by the target neurons or a unit responsive to the patient or clinician can be coupled to the control unit or microdrive motor system. The measurement device, user, or clinician can indicate a response by the target muscles or other tissues to the stimulation or recording electrode(s) to further identify the target neurons and facilitate positioning of the stimulation electrode(s). For example, if the target neurons are directed to a muscle experiencing tremors, a measurement device can be used to observe the muscle and indicate changes in tremor frequency or amplitude in response to stimulation of neurons. Alternatively, the patient or clinician may observe the muscle and provide feedback.

The lead 100 for deep brain stimulation can include stimulation electrodes, recording electrodes, or both. In at least some embodiments, the lead is rotatable so that the stimulation electrodes can be aligned with the target neurons after the neurons have been located using the recording electrodes.

Stimulation electrodes may be disposed on the circumference of the lead to stimulate the target neurons. Stimulation electrodes may be ring-shaped so that current projects from each electrode equally in every direction at any given length along the axis of the lead. To achieve current steering, segmented electrodes can be utilized additionally or alternatively. Though the following description discusses stimulation electrodes, it will be understood that all configurations of the stimulation electrodes discussed may be utilized in arranging recording electrodes as well.

Figure 1A:
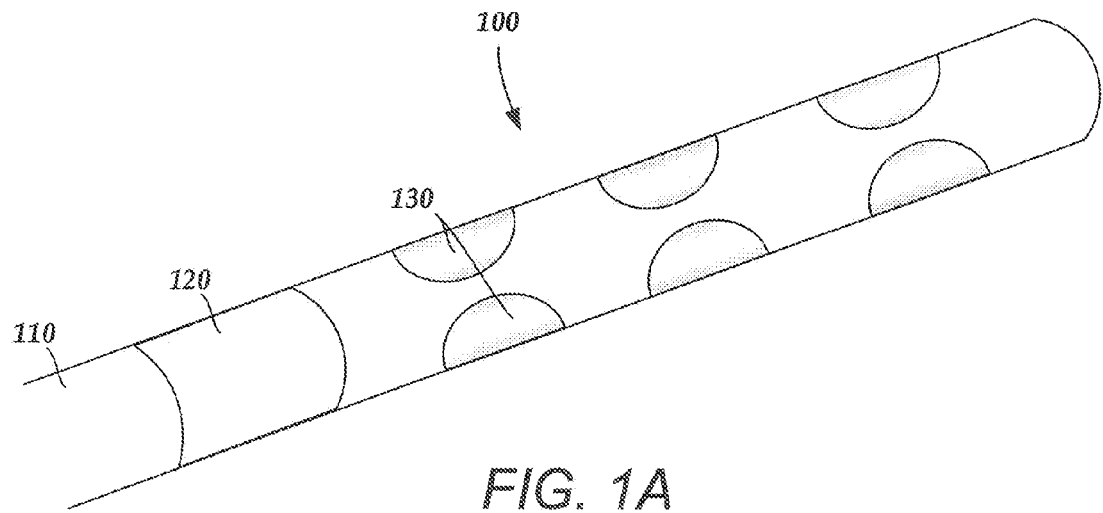
FIG. 1A is a schematic perspective view of one embodiment of a portion of a lead having a plurality of segmented electrodes and a ring electrode, according to the invention.

FIG. 1A illustrates one embodiment of a lead 100 for brain stimulation. The device includes a lead body 110, one or more ring electrodes 120, and a plurality of segmented electrodes 130. The lead body 110 can be formed of a biocompatible, non-conducting material such as, for example, a polymeric material. Suitable polymeric materials include, but are not limited to, silicone, polyurethanes, polyethylene, polyureas, or polyurethane-ureas. In at least some instances, the lead may be in contact with body tissue for extended periods of time. In at least some embodiments, the lead has a cross-sectional diameter of no more than 1.5 mm and may be in the range of 0.75 to 1.5 mm. In at least some embodiments, the lead has a length of at least 10 cm and the length of the lead may be in the range of 25 to 70 cm.

Stimulation electrodes may be disposed on the lead body 110. These stimulation electrodes may be made using a metal, alloy, conductive oxide, or any other suitable conductive material. Examples of suitable materials include, but are not limited to, platinum, platinum iridium alloy, iridium, stainless steel, titanium, or tungsten. Preferably, the stimulation electrodes are made of a material that is biocompatible and does not substantially corrode under expected operating conditions in the operating environment for the expected duration of use.

In at least some embodiments, any of the electrodes can be used as an anode or cathode and carry anodic or cathodic current. In some instances, an electrode might be an anode for a period of time and a cathode for a period of time. In other embodiments, the identity of a particular electrode or electrodes as an anode or cathode might be fixed.

The lead contains a plurality of segmented electrodes 130. Any number of segmented electrodes 130 may be disposed on the lead body 110. In some embodiments, the segmented electrodes 130 are grouped in sets of segmented electrodes, each set disposed around the circumference of the lead at or near a particular longitudinal position. The lead may have any number of sets of segmented electrodes. In at least some embodiments, the lead has one, two, three, four, five, six, seven, or eight sets of segmented electrodes. In at least some embodiments, each set of segmented electrodes contains the same number of segmented electrodes 130. In some embodiments, each set of segmented electrodes contains three segmented electrodes 130. In at least some other embodiments, each set of segmented electrodes contains two, four, five, six, seven or eight segmented electrodes. The segmented electrodes 130 may vary in size and shape. For example, in FIG. 1B, the segmented electrodes 130 are shown as circular portions. In some other embodiments, the segmented electrodes 130 are curved square portions. The shape of the segmented electrodes 130 may also be substantially triangular, diamond-shaped, oval, rectangular or spherical. In some embodiments, the segmented electrodes 130 are all of the same size, shape, diameter, width or area or any combination thereof. In some embodiments, the segmented electrodes of each set (or even all segmented electrodes) may be identical in size and shape.

In at least some embodiments, each set of segmented electrodes 130 may be disposed around the circumference of the lead body 110 to form a substantially or approximately cylindrical shape around the lead body 110. The spacing of the segmented electrodes 130 around the circumference of the lead body 110 may vary. In at least some embodiments, equal spaces, gaps or cutouts are disposed between each segmented electrodes 130 around the circumference of the lead body 110. In other embodiments, the spaces, gaps or cutouts between segmented electrodes may differ in size or shape. In other embodiments, the spaces, gaps, or cutouts between segmented electrodes may be uniform for a particular set of segmented electrodes or for all sets of segmented electrodes. The segmented electrodes 130 may be positioned in irregular or regular intervals around the lead body 110.

Stimulation electrodes in the form of ring electrodes 120 may be disposed on any part of the lead body 110, usually near a distal end of the lead. FIG. 1A illustrates a portion of a lead having one ring electrode. Any number of ring electrodes may be disposed along the length of the lead body 110. For example, the lead body may have one ring electrode, two ring electrodes, three ring electrodes or four ring electrodes. In some embodiments, the lead will have five, six, seven or eight ring electrodes. Other embodiments do not include ring electrodes.

In some embodiments, the ring electrodes 120 are substantially cylindrical and wrap around the entire circumference of the lead body 110. In some embodiments, the outer diameter of the ring electrodes 120 is substantially equal to the outer diameter of the lead body 110. Furthermore, the width of ring electrodes 120 may vary according to the desired treatment and the location of the target neurons. In some embodiments the width of the ring electrode 120 is less than or equal to the diameter of the ring electrode 120. In other embodiments, the width of the ring electrode 120 is greater than the diameter of the ring electrode 120.

Conductors (not shown) that attach to or from the ring electrodes 120 and segmented electrodes 130 also pass through the lead body 110. These conductors may pass through the material of the lead or through a lumen defined by the lead. The conductors are presented at a connector for coupling of the electrodes to a control unit (not shown). The conductors may be coupled to a control unit to provide stimulation signals, often in the form of pulses, to the stimulation electrodes.

Figure 1B:
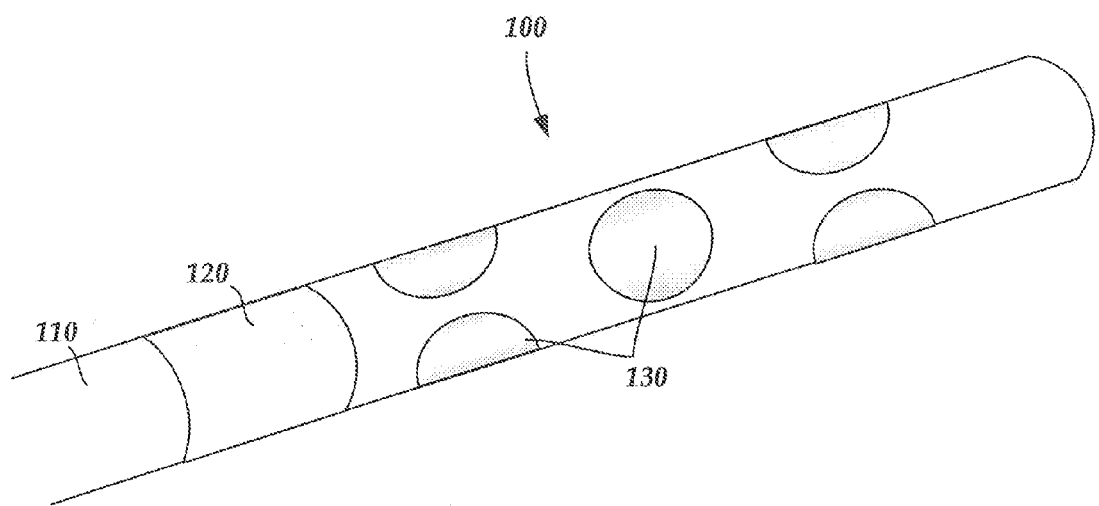
FIG. 1B is a schematic perspective view of another embodiment of a lead having a ring electrode and a plurality of segmented electrodes arranged in staggered orientation, according to the invention.

FIG. 1B is a schematic perspective view of another embodiment of a lead having a plurality of segmented electrodes. As seen in FIG. 1B, the plurality of segmented electrodes 130 may be arranged in different orientations relative to each other. In contrast to FIG. 1A, where the three sets of segmented electrodes are aligned along the length of the lead body 110, FIG. 1B displays another embodiment in which the three sets of segmented electrodes 130 are staggered. In at least some embodiments, the sets of segmented electrodes are staggered such that no segmented electrodes are aligned along the length of the lead body 110. In some embodiments, the segmented electrodes may be staggered so that at least one of the segmented electrodes is aligned with another segmented electrode of a different set, and the other segmented electrodes are not aligned.

Any number of segmented electrodes 130 may be disposed on the lead body 110 in any number of sets. FIGS. 1A and 1B illustrate embodiments including three sets of segmented electrodes. These three sets of segmented electrodes 130 may be disposed in different configurations. For example, three sets of segmented electrodes 130 may be disposed on the distal end of the lead body 110, distal to a ring electrode 120. Alternatively, three sets of segmented electrodes 130 may be disposed proximal to a ring electrode 120. By varying the location of the segmented electrodes 130, different coverage of the target neurons may be selected. For example, a specific configuration may be useful if the physician anticipates that the neural target will be closer to the distal tip of the lead body 110, while another arrangement may be useful if the physician anticipates that the neural target will be closer to the proximal end of the lead body 110. In at least some embodiments, the ring electrodes 120 alternate with sets of segmented electrodes 130.

Any combination of ring electrodes 120 and segmented electrodes 130 may be disposed on the lead. In some embodiments the segmented electrodes are arranged in sets. For example, a lead may include a first ring electrode 120, two sets of segmented electrodes, each set formed of three segmented electrodes 130, and a final ring electrode 120 at the end of the lead. This configuration may simply be referred to as a 1-3-3-1 configuration. It may be useful to refer to the electrodes with this shorthand notation. Other eight electrode configurations include, for example, a 2-2-2-2 configuration, where four sets of segmented electrodes are disposed on the lead, and a 4-4 configuration, where two sets of segmented electrodes, each having four segmented electrodes 130 are disposed on the lead. In some embodiments, the lead will have 16 electrodes. Possible configurations for a 16-electrode lead include, but are not limited to 4-4-4-4, 8-8, 3-3-3-3-3-1 (and all rearrangements of this configuration), and 2-2-2-2-2-2-2-2.

Figure 2:
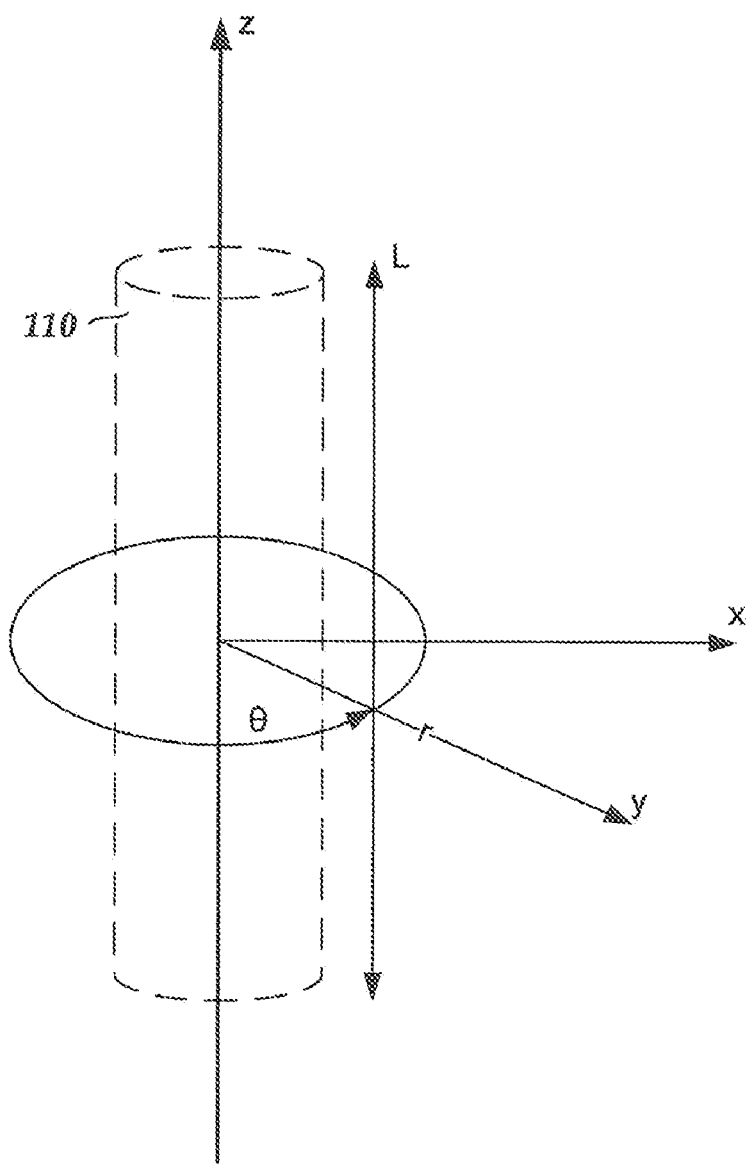
FIG. 2 is a schematic diagram of radial current steering along various electrode levels along the length of a lead, according to the invention.

FIG. 2 is a schematic diagram to illustrate radial current steering along various electrode levels along the length of a lead. While conventional lead configurations with ring electrodes are only able to steer current along the length of the lead (the z-axis), the segmented electrode configuration is capable of steering current in the x-axis, y-axis as well as the z-axis. Thus, the centroid of stimulation may be steered in any direction in the three-dimensional space surrounding the lead body 110. In some embodiments, the radial distance, r, and the angle θ around the circumference of the lead body 110 may be dictated by the percentage of anodic current (recognizing that stimulation predominantly occurs near the cathode, although strong anodes may cause stimulation as well) introduced to each electrode as will be described in greater detail below. In at least some embodiments, the configuration of anodes and cathodes along the segmented electrodes 130 allows the centroid of stimulation to be shifted to a variety of different locations along the lead body 110.

As can be appreciated from FIG. 2, the centroid of stimulation can be shifted at each level along the length of the lead. The use of multiple sets of segmented electrodes 130 at different levels along the length of the lead allows for three-dimensional current steering. In some embodiments, the sets of segmented electrodes 130 are shifted collectively (i.e. the centroid of simulation is similar at each level along the length of the lead). In at least some other embodiments, each set of segmented electrodes 130 is controlled independently. Each set of segmented electrodes may contain two, three, four, five, six, seven, eight or more segmented electrodes. It will be understood that different stimulation profiles may be produced by varying the number of segmented electrodes at each level. For example, when each set of segmented electrodes includes only two segmented electrodes, uniformly distributed gaps (inability to stimulate selectively) may be formed in the stimulation profile. In some embodiments, at least three segmented electrodes 130 are utilized to allow for true 360° selectivity.

In addition to 360° selectivity, a lead having segmented electrodes may provide several advantages. First, the lead may provide for more directed stimulation, as well as less "wasted" stimulation (i.e. stimulation of regions other than the target region). By directing stimulation toward the target tissue, side effects may be reduced. Furthermore, because stimulation is directed toward the target site, the battery in an implantable pulse generator may last for a longer period of time between recharging.

As previously indicated, the foregoing configurations may also be used while utilizing recording electrodes. In some embodiments, measurement devices coupled to the muscles or other tissues stimulated by the target neurons or a unit responsive to the patient or clinician can be coupled to the control unit or microdrive motor system. The measurement device, user, or clinician can indicate a response by the target muscles or other tissues to the stimulation or recording electrodes to further identify the target neurons and facilitate positioning of the stimulation electrodes. For example, if the target neurons are directed to a muscle experiencing tremors, a measurement device can be used to observe the muscle and indicate changes in tremor frequency or amplitude in response to stimulation of neurons. Alternatively, the patient or clinician may observe the muscle and provide feedback.

Radially segmented electrode arrays may be manufactured in a variety of ways. In at least some embodiments, a cable system disposed within the lead is used to position and attach the segmented electrodes. The cable system may be modified to couple different numbers of segmented electrodes, to adjust the radial spacing between segmented electrodes or to vary the longitudinal position between levels of segmented electrodes.

Figure 3:
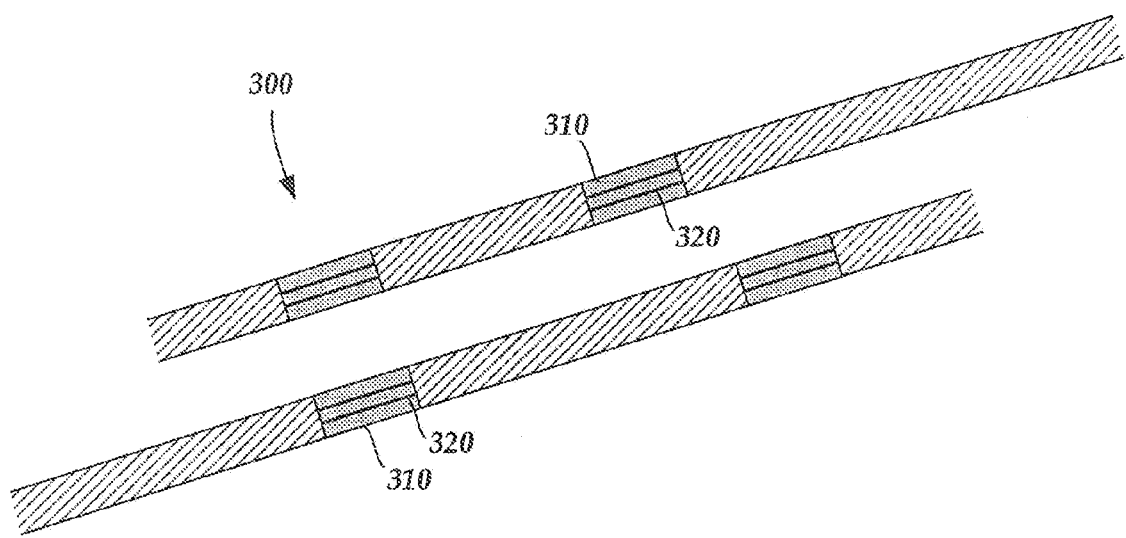
FIG. 3 is a schematic perspective view of one embodiment of portions of longitudinal cables having a plurality of ablated sections, according to the invention.

FIG. 3 is a schematic perspective view of one embodiment of a longitudinal cable 300. The longitudinal cable 300 may include conductors disposed within the insulative or non-conductive material. The conductors may also be disposed along the cable. In some embodiments, the longitudinal cable 300 runs the length of the lead. In at least some other embodiments, the longitudinal cable 300 is an elongate member that runs the length of a portion of the distal end of the lead where the segmented electrodes are to be attached. The longitudinal cables 300 may be disposed through the center of the lead. In some embodiments, multiple longitudinal cables 300 may be disposed within the lead such that they appear as a ring within the lead when a cross-section of the lead is viewed. In some embodiments, each longitudinal cable 300 is a linear member that extends throughout the lead. It will be understood that the longitudinal cables 300 may instead be formed of flexible members that wind, twist or coil within the lead.

FIG. 3 shows two longitudinal cables 300, though it will be understood that any number of longitudinal cables 300 may be used. In some embodiments, one, two, three, four, five, six, seven or eight longitudinal cables 300 are utilized. The longitudinal cables 300 may be disposed in parallel within the lead. Alternatively, the longitudinal cables 300 may be intertwined, twisted or braided. In at least some embodiments, the longitudinal cables 300 are separated, particularly at the distal end of the lead, such that each longitudinal cable 300 includes adequate spacing for the electrodes to attach to the cables.

The longitudinal cables 300 may include ablated sections 310 for attachment of the electrodes. In FIG. 3, each longitudinal cable 300 includes two ablated sections 310 though it will be understood that each longitudinal cable 300 may include any number of ablated sections 310 (e.g. one, two, three, four, five, or six). The number of ablated sections 310 may be the same or different on each longitudinal cables 300. In some embodiments, each ablated section 310 corresponds to a single segmented electrode. In some embodiments, the ablated sections 310 will correspond to the position of the segmented electrodes (not shown). Thus, ablated sections 310 may be disposed at predetermined distances on the surface of the longitudinal cables 300. In some embodiments, the distance is the same between each ablated section 310 along the length a longitudinal cable 300. In some embodiments, the same distance between ablated sections 310 is used on all the longitudinal cables 300.

As described above, conductors 320 may be coupled to segmented electrodes to provide stimulation signals or to relay recorded signals. In some embodiments, the conductors 320 are disposed within the longitudinal cables 300. Each longitudinal cable 300 may house a single conductor 320 that extends throughout the longitudinal cable 300. In at least some embodiments, multiple conductors 320 are disposed within the longitudinal cables 300. For example, in some embodiments, the number of conductors 320 corresponds to the number of segmented electrodes that are coupled to the longitudinal cable 300, one conductor 320 for each segmented electrode. In embodiments having multiple conductors 320, the conductors 320 may extend throughout the longitudinal cable 300, but separated from each other. Furthermore, by providing ablated sections 310, the segmented electrodes may be attached to the conductors 320, which are housed within the longitudinal cable 300, as will be described with reference to FIG. 6.

Figure 4A:
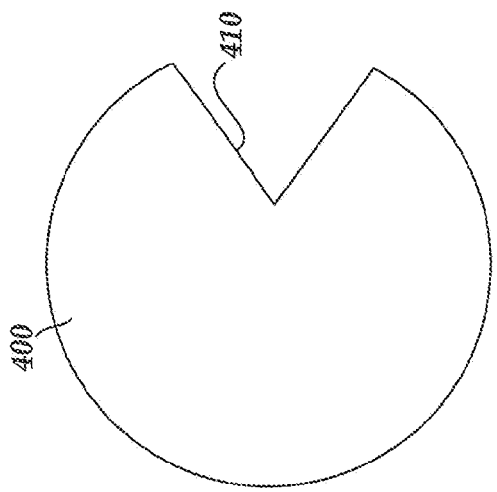
FIG. 4A is a schematic top view of a first embodiment of a spherical electrode having a cutout portion in the form of a groove, according to the invention.

The segmented electrodes can have a variety of different shapes and sizes. FIG. 4A is a schematic top view of one embodiment of a spherical electrode 400 having a cutout portion 410. As seen in FIG. 4A, a segmented electrode may be formed as a portion of a spherical, or substantially spherical, body made of a material selected from metal, alloy, conductive oxide, or any other suitable conductive material. In some embodiments only a portion of a spherical body is used to create the segmented electrode 400. In at least some other embodiments, the segmented electrodes are formed of a portion of a cuboid, a cube, a cylinder, a cone, a triangular prism or a pyramid.

In FIG. 4A, a whole spherical body (less the cutout portion 410) is used to create the electrode. The electrode 400 may be formed of any suitable size. In some embodiments, a plurality of spherical electrodes are disposed on a lead, all having the same size. Alternatively, different longitudinal cables 300 may include electrodes 400 of different sizes. Alternatively, electrodes 400 may increase or decrease in size from the proximal to the distal end of a lead.

As seen in FIG. 4A, the spherical electrodes 400 defines a cutout portion 410. The cutout portion 410 may be useful in coupling the electrode 400 to one of the longitudinal cables 300. Specifically, the use of a cutout portion 410 may facilitate manufacturing leads having stronger attachments between the conductors and the electrodes 400. For example, the conductors and electrodes 400 may be crimped or welded within the cutout portions 410. A stronger attachment may in turn reduce the risk of lead failure and lead breakage when the lead is being inserted into the body or during use. In FIG. 4A, the cutout portion 410 is in the form of a lateral groove. As can be appreciated from FIG. 4A, the cutout portion 410 may extend across the electrode 400 in order to couple it with the longitudinal cable 300.

Figure 4B:
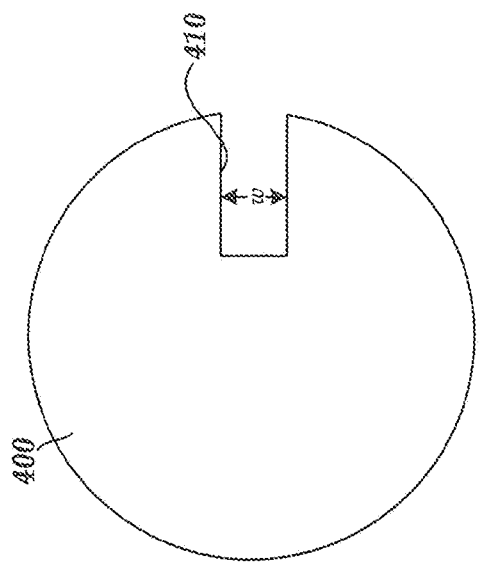
FIG. 4B is a schematic top view of a second embodiment of a spherical electrode having a cutout portion in the form of a rectangular cutout, according to the invention.
Figure 4C:
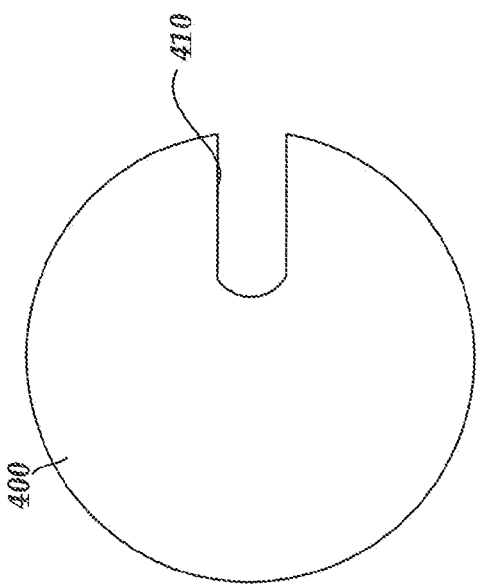
FIG. 4C is a schematic top view of a third embodiment of a spherical electrode having a cutout portion in the form of a triangular cutout, according to the invention.

It will be understood that the cutout portion 410 may be formed in a variety of shapes and sizes. For example, FIG. 4B shows a second embodiment of an electrode 400 having a cutout portion 410 in the form of a rectangular cutout. FIG. 4C shows a third embodiment of an electrode 400 having a cutout portion 410 in the form of a triangular cutout. As can be appreciated, any suitable shape or size may be used for the cutout portion 410 in order to achieve coupling between the electrode 400 and the longitudinal cable 300. In some embodiments, the size and shape of the cutout portion 410 is configured such that one of the conductors 320 is brought in contact with the electrode 400. In at least some embodiments, the width, w, of the cutout portion 410 corresponds to the diameter of the ablated section 310 of the longitudinal cable 300 or to the diameter of one of the conductors within the longitudinal cable 300.

In some embodiments, it may be desirable to have an isodiametric lead. In such embodiments, a spherical electrode 400 may be disposed on the longitudinal cable and later ground down to the appropriate radial level. Alternatively, a portion of a sphere may be used to create a partially-spherical electrode 500 as illustrated, for example, in FIGS. 5A and 5B.

It will be understood that the partially-spherical electrodes 500 described herein may be used instead of the spherical electrodes 400. Furthermore, embodiments using a combination of spherical and partially-spherical electrodes may be constructed.

Figure 5A:
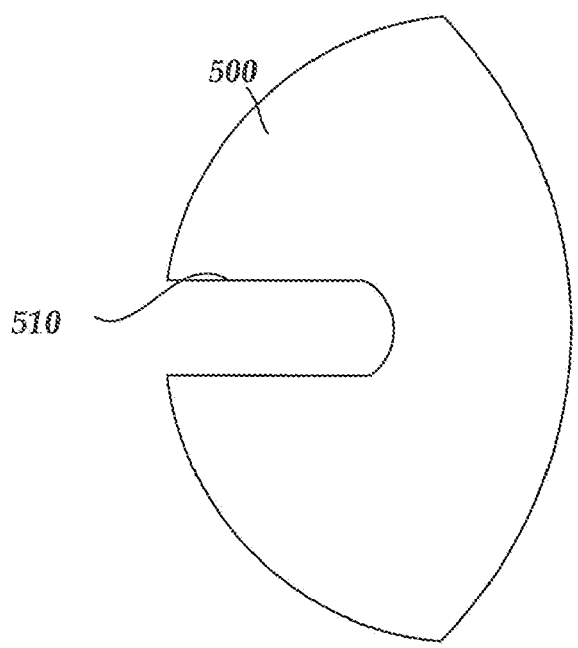
FIG. 5A is a schematic top view of one embodiment of a partially-spherical electrode, according to the invention.
Figure 5B:
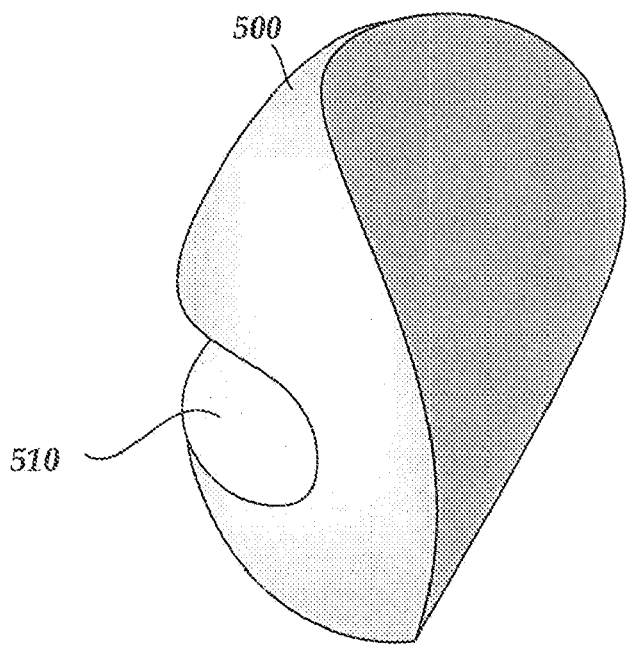
FIG. 5B is a schematic perspective view of the partially-spherical electrode of FIG. 5A, according to the invention.

FIG. 5A is a schematic top view of an embodiment of a partially-spherical electrode 500, and FIG. 5B is a schematic perspective view of the partially-spherical electrode 500 of FIG. 5A. As can be appreciated from these figures, the electrodes that will be disposed on the longitudinal cable need not be formed of whole spheres as illustrated in FIGS. 4A-C. Instead, only a portion of a sphere may be used to form the electrode. In some embodiments, the partially-spherical electrode 500 may be hemispherical. It will be understood, that any portion of a sphere may be used to form the partially-spherical electrode 500 (e.g. one-half, one-third, one-fourth, or one-eighth of a sphere).

The partially-spherical electrode 500 also includes a cutout portion 510. The cutout portions 410 may be the same as those described above in reference to the spherical electrodes 400. Opposite the cutout portion 510, the partially-spherical electrode 500 may include an outer surface having a curvature matching the final curvature of the lead body. Thus, a partially-spherical electrode 500 may be formed in this manner so that no further grinding of the partially-spherical electrode 500 is necessary to create an isodiametric lead. The partially-spherical electrode 500 may also be the result of grinding or cutting a portion of a surface from an original electrode precursor.

Figure 6:
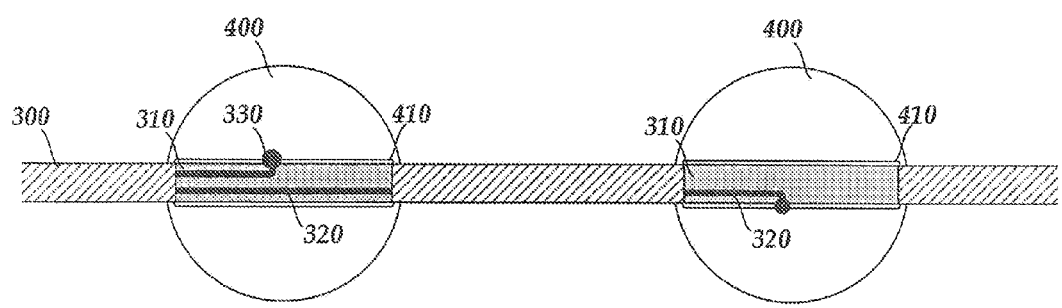
FIG. 6 is a cross-sectional schematic view of one embodiment of a plurality of spherical electrodes disposed on a portion of a longitudinal cable, according to the invention.

FIG. 6 is a cross-sectional schematic view of one embodiment of a plurality of electrodes 400 disposed on a portion of a longitudinal cable 300. As seen in FIG. 6, an electrode 400 may be coupled to the longitudinal cable 300 at the site of an ablated section 310. Specifically, the cutout portion 410 of the electrode 400 may be coupled to the ablated section 310 of the longitudinal cable 300. As can be appreciated from FIG. 6, each electrode 400 may be brought in contact with a conductor 320 disposed within the longitudinal cable 300 via the ablated section 310 and cutout portion 410. The ablated section 310 of the longitudinal cable 300 may be disposed within the cutout portion 410 so that a conductor 320 is electrically coupled to the electrode 400.

Any suitable method of coupling or securing the electrodes 400 to the longitudinal cables 300 may be used. In some embodiments, the ablated section or a conductor is inserted into a cutout portion of an electrode and the electrode 400 is crimped onto the ablated section 310 of the longitudinal cable 300. In some embodiments, the electrodes 400 are welded onto the ablated section 310 of the longitudinal cable 300. Specifically, an electrode 400 may also be welded to a conductor 320 as seen in FIG. 6. Welding of the electrode 400 to the conductors 320 may be done at a single point of welding 330 or at multiple points along the length of the conductor for added stability. In some embodiments, an electrode 400 is welded onto the longitudinal cable and then crimped on an ablated section 310 of the longitudinal cable 300.

Though FIG. 6 only illustrates two electrodes 400, it will be understood that any number of spherical electrodes 400 or partially-spherical electrodes 500 may be disposed on each longitudinal cable 300. Additionally, though FIG. 6 illustrates spherical electrodes 400 disposed in the same orientation, the spherical electrodes 400 may be positioned in different orientations. For example, FIG. 6 illustrates an embodiment in which both cutout portions 410 are facing the same direction. Alternatively, the spherical electrode 400 may be rotated about the longitudinal cable 300 such that the spherical electrodes 400 engage the longitudinal cable 300 at different angles. As will be appreciated by one of ordinary skill in the art, the radial positioning of the electrode about the longitudinal cable 300 may be significant when partially-spherical electrodes 500 are disposed about the longitudinal cable 300.

Figure 7:
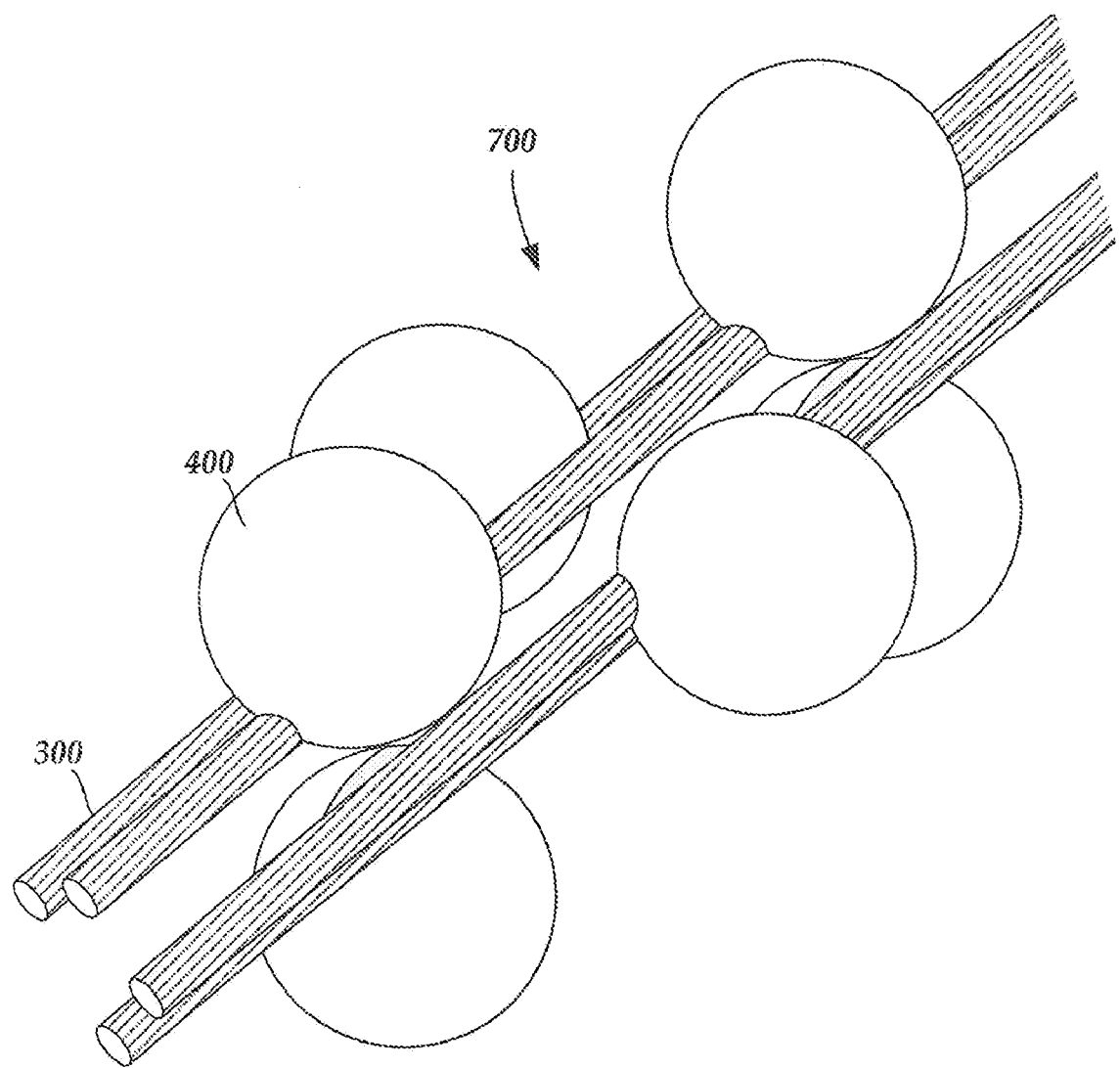
FIG. 7 is a schematic perspective view of one embodiment of a plurality of longitudinal cables, each having a plurality of spherical electrodes, according to the invention.

FIG. 7 is a schematic perspective view of one embodiment of a plurality of longitudinal cables 300, each having a plurality of spherical electrodes 400. As seen in FIG. 7, the longitudinal cables 300 and spherical electrodes 400 may be arranged such that there is ample spacing between the spherical electrodes 400. In some embodiments, the resulting lead will have levels or rows of spherical electrodes 400 with varying numbers of spherical electrodes are disposed at each longitudinal level. Additionally, the levels may be configured to have different-sized spherical electrodes 400 at different longitudinal levels.

Figure 8:
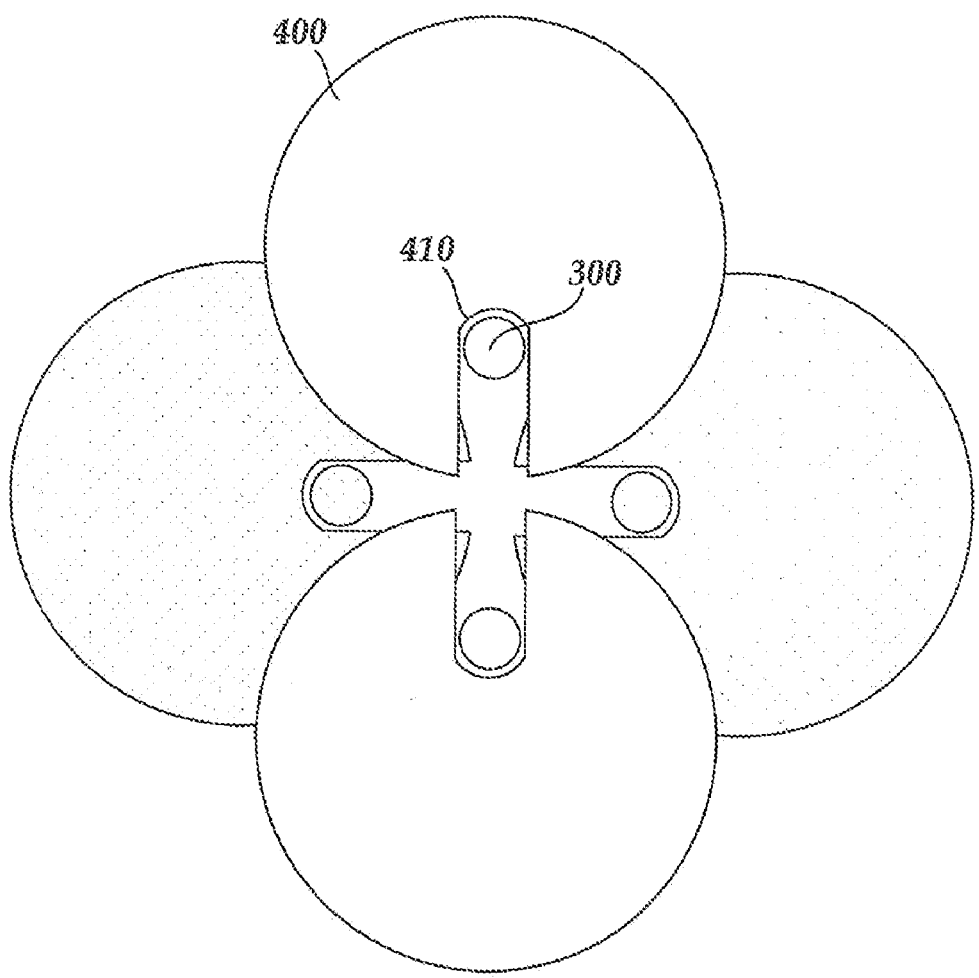
FIG. 8 is a schematic top view of one embodiment of a plurality of longitudinal cables, each having a spherical electrode, according to the invention.

FIG. 8 is a schematic top view of one embodiment of a plurality of longitudinal cables 300, each having a spherical electrode 400. The spherical electrodes 400 are disposed at longitudinal positions such that there are two spherical electrodes 400 at each longitudinal level of the lead, though any number of spherical electrodes 400 may be disposed at each level. The spherical electrodes 400 may be arranged, each opposing the other. As seen in FIG. 8, four longitudinal cables 300 are used. It will be appreciated by one of ordinary skill in the art, that any number of longitudinal cables 300 may be used. For example, by modifying the shape of the spherical electrodes 400 and the cutout portions 410, the four longitudinal cables 300 may be replaced by three, two or a single longitudinal cable disposed in the center of the four spherical electrodes 400.

Figure 9:
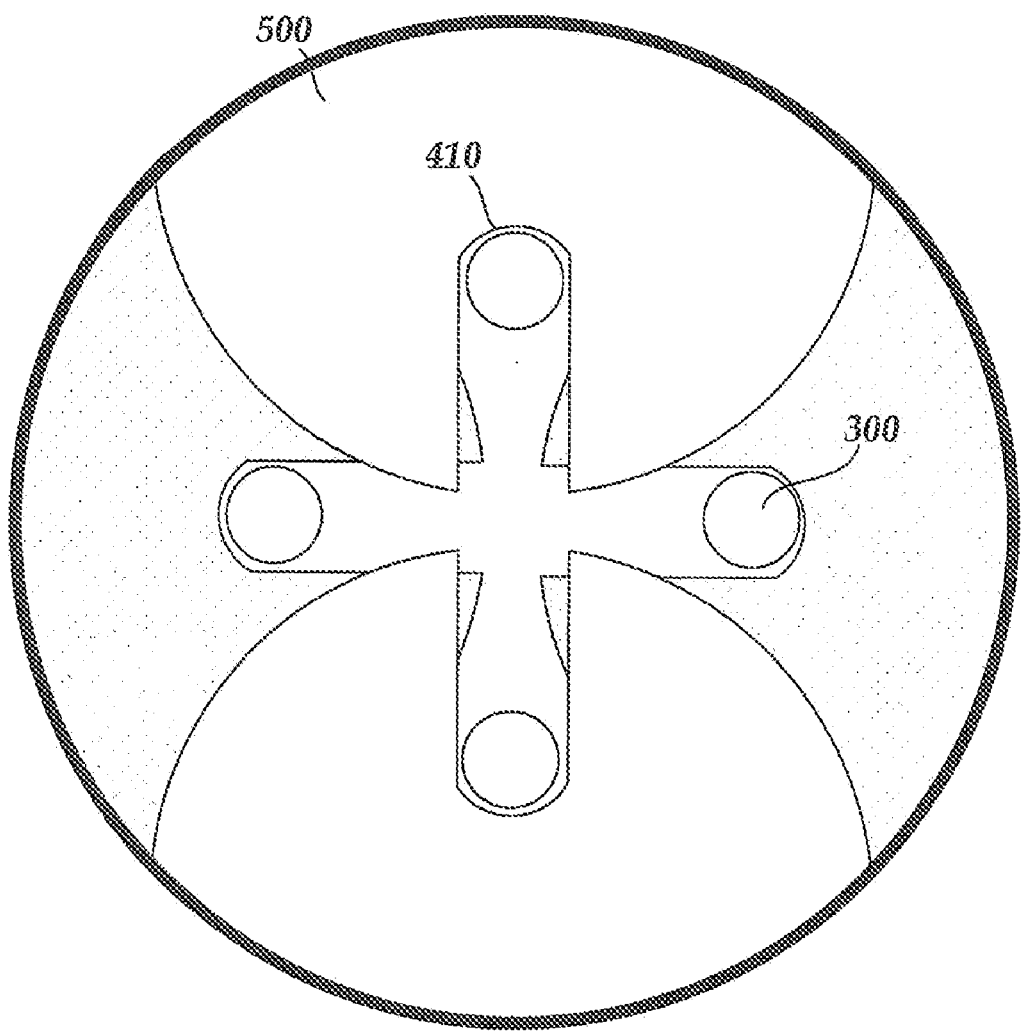
FIG. 9 is a schematic top view of one embodiment of a plurality of longitudinal cables, each having a partially-spherical electrode, according to the invention.

FIG. 9 is a schematic top view of one embodiment of a plurality of longitudinal cables 300, each having a partially-spherical electrode 500. The partially-spherical electrodes 500 may be similar to those described with reference to FIGS. 5A and 5B. As can be appreciated from FIG. 9, when the partially-spherical electrodes 500 are properly disposed on the longitudinal cables 300 a lead may be formed without having to grind down the partially-spherical electrodes. In this case, when a lead body is formed about the assembly 700, an isodiametric lead is readily formed.

Figure 10:
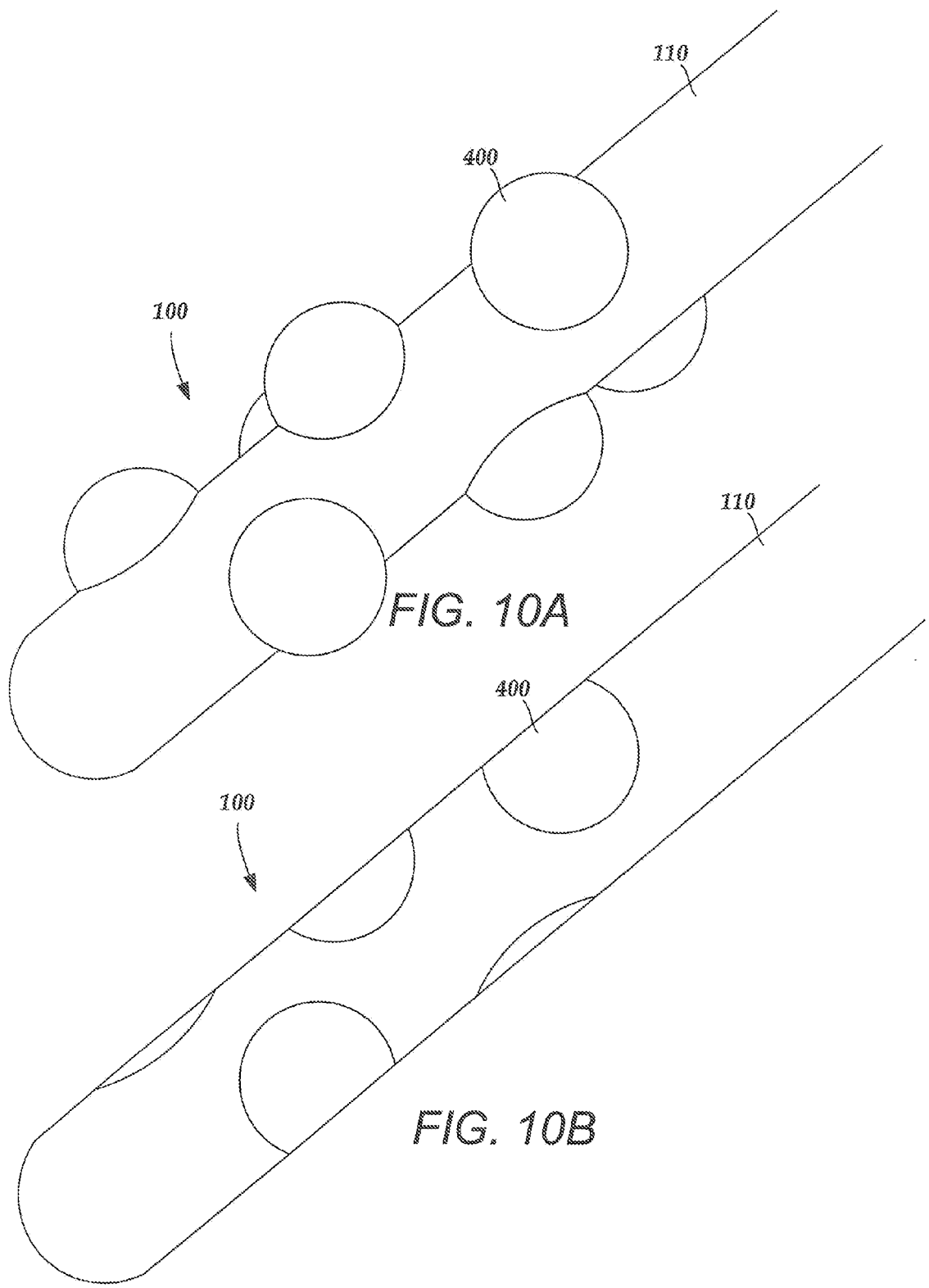
FIG. 10A is a schematic perspective view of one embodiment of a lead having a plurality of spherical electrodes, according to the invention.
FIG. 10B is a schematic perspective view of the lead of FIG. 10A after grinding, according to the invention.

FIG. 10A is a schematic perspective view of one embodiment of a lead 100 having a plurality of electrodes 400. The assembly 700 of FIG. 7 may be placed into a liquid injection mold to create the lead body 110. First, the assembly 700 may be placed in the desired array arrangement by positioning it in a mold. Suitable materials for the mold include, but are not limited to metal, polymers (including plastics), composite materials, and the like. Preferably, the mold is made of a durable material that allows the mold to be reused.

After the assembly 700 is positioned in the mold, a mold cover may be placed over the assembly 700. A lead body may then be formed by any process including, for example, molding (including injection molding), casting, and the like. In some embodiments, the lead body is formed by injection molding. In this manner, a lead body 110 may be formed around the assembly 700 to create a lead 100.

As can be appreciated from FIG. 10A, because of the shape and arrangement of the spherical electrodes 400, portions of the spherical electrodes 400 project out of the lead 100 after the creation of the lead body 110. In some embodiments, an isodiametric lead may be useful. In these embodiments, the lead 100 may be ground down so that the spherical electrodes 400 are flush with the lead body 110. In some embodiments, the lead 100 is ground down using center grinding. FIG. 10B is a schematic perspective view of the lead of FIG. 10A after the grinding process. The resulting lead 100 includes spherical electrodes 400 having the shape of circular electrodes disposed about the surface of the lead 100. Furthermore, each of these spherical electrodes 400 are electrically coupled to connectors on the inside of the lead 100. The grinding process may be minimized or eliminated using partially-spherical electrodes 500 in place of spherical electrodes 400.

Figure 11:
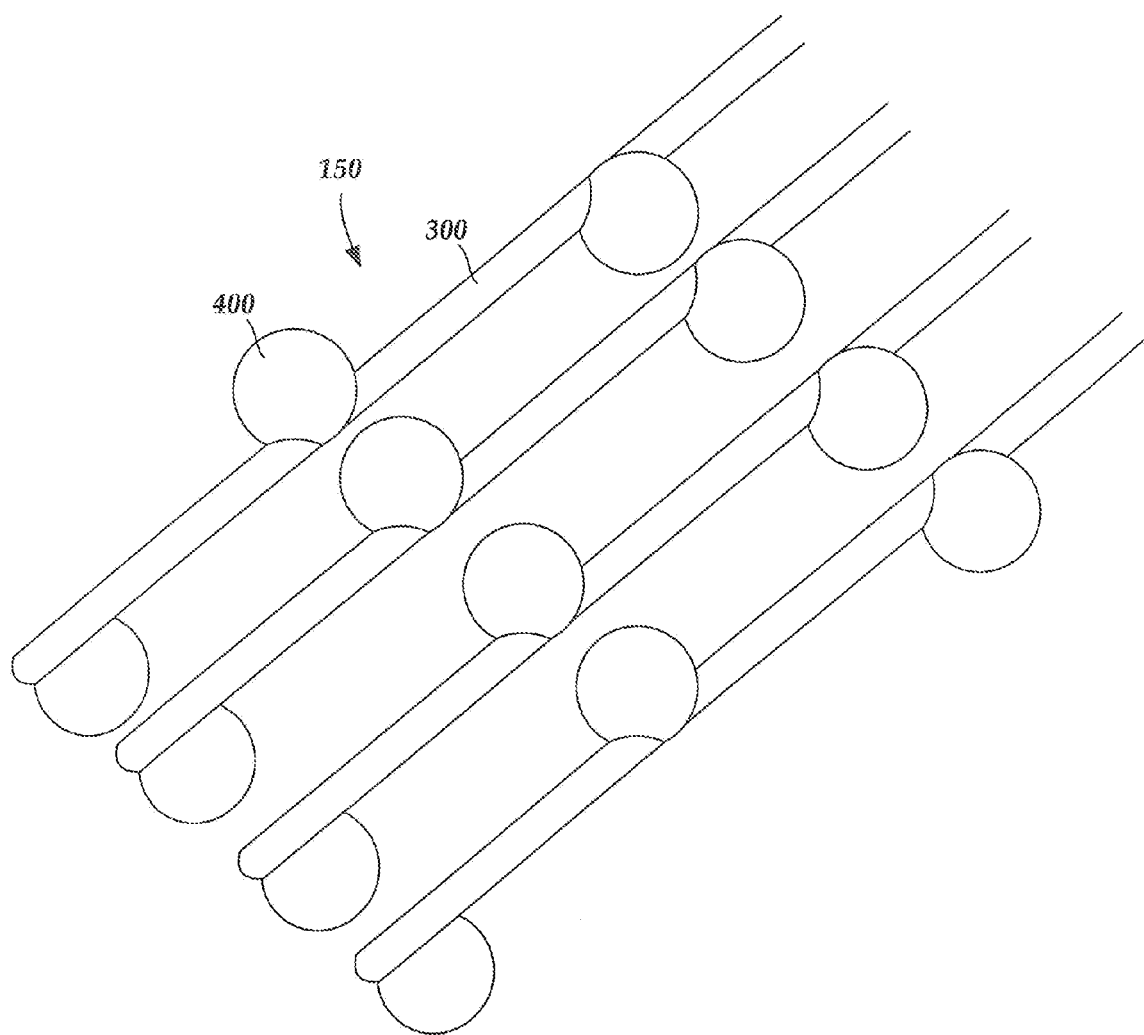
FIG. 11 is a schematic perspective view of one embodiment of a lead having a plurality of stimulating units, according to the invention.

FIG. 11 is a schematic perspective view of one embodiment of a lead 100 having a plurality of stimulating units 150. Each stimulating unit 150 may include a longitudinal cable 300 and a plurality of spherical electrodes 400. It will be understood that partially-spherical electrodes 500 may also be used in combination with this embodiment. The stimulating unit 150 may be manufactured by molding each stimulating unit 150 separately within a mold. In some embodiments, each stimulating unit 150 may be in the form of individual fingers so as to be operated separately and independently. Thus, the lead 100 may be formed to have a plurality of independently-operating stimulation units 150. Within each longitudinal cable, a plurality of conductors 330 may be disposed so that each spherical electrode 400 is operated independently. In this manner, the parameters of stimulation, such as frequency, duration and amplitude may be varied from one spherical electrode 400 to the next. Additionally, each individual stimulation unit 150 may be ground down as described with reference to FIG. 10B so that each stimulation unit 150 is isodiametric. In some embodiments, the stimulation units 150 are of the same length. Furthermore, in some embodiments, the stimulation units 150 of the lead 100 are joined at the proximal end into a single lead body.

Modifications of these methods are possible. For example, two or more of these methods may be used in combination to provide leads having both spherical and partially-spherical electrodes. Furthermore, by varying the size and shape of the electrodes, it may be possible to produce leads having different stimulation and recording advantages. In some embodiments, these methods are used with lead constructions other than deep brain stimulation leads.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A lead for brain stimulation, comprising:
a cylindrical lead body having a distal end and a circumference;
at least one cable extending within the lead body, each cable comprising at least one conductor; and
a plurality of electrodes coupled to the at least one cable and disposed along the distal end, and distributed around the circumference, of the cylindrical lead body, each of the plurality of electrodes defining a cutout portion that receives and attaches to a one of the at least one cable.

2. The lead of claim 1, wherein each of the plurality of electrodes has an exterior surface corresponding to at least a portion of a sphere.

3. The lead of claim 2, wherein each of the plurality of electrodes has a shape corresponding to a full sphere having a cutout portion.

4. The lead of claim 1, wherein the at least one cable and the plurality of electrodes comprise a first cable and a first electrode, respectively, the first cable comprising a first conductor and an ablated section exposing a portion of the first conductor, wherein at least a portion of the ablated section is disposed within the cutout portion of the first electrode with electrical coupling of the exposed portion of the first conductor to the first electrode.

5. The lead of claim 1, wherein the cutout portion comprises a groove having a diameter corresponding to a diameter of the at least one conductor.

6. The lead of claim 1, wherein each of the at least one cable is coupled to at least two of the plurality of electrodes.

7. The lead of claim 1, wherein at least two of the plurality of electrodes are disposed at a same longitudinal position on the lead body.

8. The lead of claim 1, wherein the plurality of electrodes are coupled to the at least one cable and disposed on the lead body so that the lead is isodiametric.

9. The lead of claim 1, wherein each of the at least one cable comprises at least two conductors disposed within the cable.

10. A lead for brain stimulation, comprising:
a plurality of stimulating units, each of the plurality of stimulating units comprising:
at least one cable extending within the lead body, each cable comprising at least one conductor; and
a plurality of electrodes coupled to the at least one cable, each of the plurality of electrodes comprising at least a portion of a sphere and a cutout portion that receives and attaches to a one of the at least one cable; and
a lead body formed about each of the plurality of stimulating units.

11. The lead of claim 10, wherein the plurality of stimulating units are coupled at the proximal end.

12. The lead of claim 10, wherein each of the plurality of stimulating units comprises the same number of the plurality of electrodes disposed at the same longitudinal position along each of the at least one cable.

13. The lead of claim 10, wherein the cutout portion comprises a groove having a diameter corresponding to a diameter of the at least one conductor.

14. An implantable stimulation device, comprising:
the lead of claim 1; and
a control module coupleable to the lead.

15. The implantable stimulation device of claim 14, wherein the implantable stimulation device is a deep brain stimulator.

16. A method of manufacturing a device for brain stimulation, the method comprising:
forming at least one cable having at least one conductor;
coupling a plurality of electrodes to the at least one cable, each of the plurality of electrodes comprising at least a portion of a sphere and defining a cutout portion that receives and attaches to a one of the at least one cable; and
forming a lead body over the at least one cable.

17. The method of claim 16, wherein coupling a plurality of electrodes comprises crimping a plurality of electrodes to the at least one cable.

18. The method of claim 16, wherein coupling a plurality of electrodes comprises welding a plurality of electrodes to the at least one cable.

19. The method of claim 16, wherein forming a lead body comprises forming a lead body through liquid injection molding.

20. The method of claim 16, further comprising grinding the plurality of electrodes so that the lead body and the plurality of electrodes are isodiametric.

* * * * *